US005750996A

United States Patent [19]
Drennen, III et al.

[11] Patent Number: 5,750,996
[45] Date of Patent: May 12, 1998

[54] APPARATUS FOR NONDESTRUCTIVELY INSPECTING A COATED ARTICLE AND ASSOCIATED METHOD

[75] Inventors: James K. Drennen, III, Mars; John D. Kirsch, Pittsburgh, both of Pa.

[73] Assignee: Duquesne University of the Holy Ghost, Pittsburgh, Pa.

[21] Appl. No.: 934,928

[22] Filed: Sep. 22, 1997

Related U.S. Application Data

[63] Continuation of Ser. No. 721,263, Sep. 26, 1996, abandoned.
[51] Int. Cl.$^6$ .................................................. G01N 21/35
[52] U.S. Cl. ............................... 250/341.2; 356/446
[58] Field of Search ................................ 356/446, 445, 356/381, 382; 250/339.11, 341.2, 341.8

[56] References Cited

U.S. PATENT DOCUMENTS

| | | | |
|---|---|---|---|
| 4,180,331 | 12/1979 | Lundstrom | 250/341.8 |
| 4,843,894 | 7/1989 | Yashiro et al. | 250/341.2 |
| 5,056,962 | 10/1991 | Morimoto et al. | 406/49 |
| 5,085,510 | 2/1992 | Mitchell | 356/237 |
| 5,170,056 | 12/1992 | Berard et al. | 250/341 |
| 5,214,277 | 5/1993 | Drennen, III | 250/216 |
| 5,278,412 | 1/1994 | DeThomas et al. | 250/339.11 |

*Primary Examiner*—F. L. Evans
*Attorney, Agent, or Firm*—Arnold B. Silverman; Eckert Seamans Cherin & Mellott, LLC

[57] ABSTRACT

Apparatus and an associated method are provided for nondestructively inspecting a coated article which may be a coated drug unit to determine the extent of coating on the exterior thereof. A probe may be received within a housing wherein the article is coated and transported as in a fluidized bed. A probe which has a recess for receiving coated article and a communicating fiberoptic receiving passageway. The recess receives a single coated article or plurality of coated articles on which light, which is preferably near-infrared light, is caused to impinge by a first group of fiberoptic fibers with the reflected light being delivered from the coated article to a spectrometer which analyzes the coating information. A microprocessor may be employed to control the inspection process, as well as the coating system. The probe may be rotatably mounted within the housing to facilitate removal of the coated article after inspection under the influence of gravity. In the alternative, suction may be employed to urge the coated article into the recess prior to and during inspection and pressure may be employed to remove the coated article from the recess after inspection. The invention also contemplates removing the coated article from the housing of the probe to permit inspection outside of the housing or use of the probe independently of the coating equipment. The coated article may be positioned and clamped in the probe during inspection.

42 Claims, 7 Drawing Sheets

FIG. 13 levels
APPARATUS FOR NONDESTRUCTIVELY INSPECTING A COATED ARTICLE AND ASSOCIATED METHOD This application is a continuation of application Ser. No. 08/721,263, filed on Sep. 26, 1996, now abandoned.

BACKGROUND OF THE INVENTION

1. Field of the Invention

The present invention relates to apparatus for nondestructively inspecting the coating on a coated article, such as a coated drug unit and, more specifically, it relates to such apparatus which may be employed in connection with the coating operation. Associated methods are also provided.

2. Description of the Prior Art

Various coating techniques have been employed to coat various articles for a wide variety of purposes. Examples of such coatings would be in connection with final pharmaceutical unit dosage forms, such as tablets or capsules, intermediate products, such as granules or pellets, or in other environments, such as coated agricultural seeds and candy in the confectionery industry. It is frequently important that the coating material be controlled precisely in order to provide an effective product. For example, in connection with drugs, coatings may be employed for functional or aesthetic purposes to mask the taste of the medication, control the rate of drug dissolution within the body, enhance the appearance of the drug, increase shelf life, and resist gastrointestinal irritation. Drug solutions or suspensions may also be layered onto granulations or inert beads (nonpareil seeds). In another use, agricultural seeds might be coated with pesticides, herbicides, or fungicides, for example. Candy and gum are often coated with sugar or other materials.

One known prior art technique for determining the extent of coating is to determine the mass of the uncoated item and the mass of the coated item with the comparison facilitating such a determination. Among the disadvantages of such an approach are that it cannot be done on-line, that it is time-consuming, and the mass, while permitting a determination of the total amount of coating present, does not take into account the differences in uncoated core mass.

U.S. Pat. No. 5,085,510 discloses a visual inspection system for inspecting pharmaceutical tablets. This system involves introducing tablets obtained from a hopper into a carrier, and transporting them by conveyor belt to photoelectric detection means which may be CCD cameras. Lighting means are employed to illuminate each tablet face. A fiberoptic light source is disclosed in one embodiment.

U.S. Pat. No. 5,056,962 discloses a sampling of solid materials, such as medical tablets moved through an inspection station by way of a transport plug which is disposed within a transport pipe.

U.S. Pat. No. 5,170,056 discloses the use of fiberoptics coupled to an infrared device for remote spectroscopy.

U.S. Pat. No. 5,214,277, which issued to one of the inventors named herein, discloses the use of near infrared reflectance spectrometry in connection with specifically configured specimen support means. This system employs a parabolic reflector to illuminate all tablet surfaces.

In spite of the foregoing disclosures, there remains a very real and substantial need for an inspection system which can effectively sample a coated article, such as a drug unit dosage form or component thereof and determine rapidly and efficiently the extent of coating.

SUMMARY OF THE INVENTION

The present invention provides apparatus for nondestructively inspecting a coated article to determine the extent of coating. It also provides means for determining other characteristics, such as granulation, drying, mixing and potency in drug layering. Also, beads, pellets and agricultural seeds, for example, may be inspected in large numbers of relatively small individual units simultaneously.

In a preferred embodiment, the apparatus includes a housing for containing and transporting the coated article. A fluidized bed, rotating pan, or other suitable system may be employed. In one embodiment, an elongated coated article receiving probe is receivable within the housing. The probe has an article receiving recess in communication with the exterior of the probe and a passageway for receiving fiberoptic means in communication with the coated article receiving recess. Spectrometer means are employed to analyze the coating thickness on the basis of information obtained by transporting near infrared light through a first group of fibers in a fiberoptic bundle causing the light to impinge upon the coated article and employing a second group of fibers to transport reflected light which is preferably diffuse reflection to the spectrometer means.

The recess is preferably of a size and shape so as to receive the coated article in intimate contact. In one preferred approach, the entry portion of the recess is enlarged to facilitate ease of entry of a coated article into the recess. The probe may be axially rotatable so as to facilitate removal of the coated article and return to the fluidized bed or other source after inspection under the influence of gravity. Pneumatic or other means may be employed to apply positive pressure to remove the coated article from the recess after inspection and may be employed to apply a vacuum to the recess in order to urge retention of the coated article in the recess prior to completion of inspection.

In one embodiment, the probe is partially or totally removable in an axial direction from the housing so as to facilitate withdrawal of a specimen for inspection at-line rather than on-line. A means for clamping the coated article to enhance the efficiency of inspection may be provided.

Microprocessor means may be employed so as to control operation of the inspection means as by controlling delivery of near infrared light, operation of the spectrometer means and, if desired, use of the information obtained from inspection in a servomechanism concept to adjust or halt the coating system.

The method of the present invention involves providing apparatus of the type described, introducing a coated article into the recess, delivering near infrared light through the fiberoptic means to the coated article and receiving reflected light from the coated article which is delivered to processing means for determining the extent of coating.

It is an object of the present invention to provide apparatus and an associated method for rapidly and efficiently effecting nondestructive inspection of a coated article to determine extent of coating.

It is a further object of the present invention to provide such a system which will receive and test a single coated article or multiple particulates or articles, such as in the case of granulations, pellets, beads, agricultural seeds, and powders, for example, obtained from a fluidized bed stream or other suitable source.

It is yet another object of the invention to provide such a system which is uniquely suited to inspecting the coating on coated drug units by means of remotely positioned spectrometer means.

It is a further object of the present invention to provide such a system wherein the inspection may be performed on-line and if the thickness is as desired, the coated article may be returned to the stream of the coated articles from which it was taken.

It is another object of the present invention to provide improved means for positioning and securing the sample during inspection.

These and other objects of the invention will be more fully understood from the following description on reference to the illustrations appended hereto.

DESCRIPTION OF THE PREFERRED EMBODIMENTS

As employed herein, the term "coated drug unit" means (a) a unit dosage of a solid pharmaceutical, such as a tablet or capsule or (b) components therefor, such as a granule, pellet, or inert bead, for example, which has an exterior coating.

As used herein, the term "coated article" means a coated drug unit or another exteriorly coated article or articles, such as, for example, agricultural seed or seeds, which may have a coating of a pesticide, a herbicide, or fungicide, or a coated confection. A coated confection may, for example, involve a sugar coating, another flavoring agent, a coloring agent, or combinations thereof.

As used herein, the term "extent of coating" means the degree to which an exterior surface has a coating material, whether desired or not, whether the coating material is continuous or discontinuous, and whether the coating material being monitored will be part of the final product. The term shall expressly include, but not be limited to determination of (a) amount of coating or (b) coating thickness.

Figure 1:
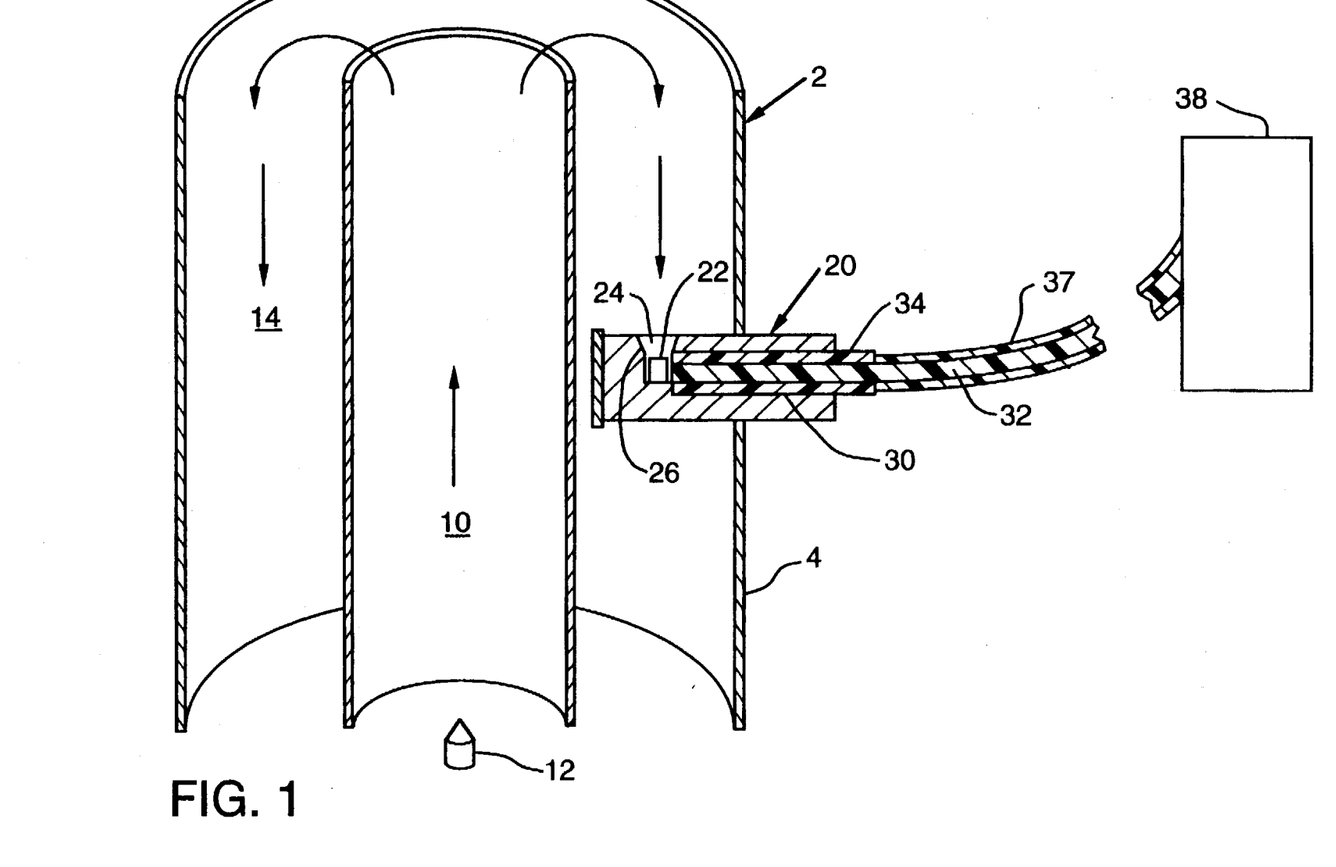
FIG. 1 is a partially schematic cross-sectional view of a coating chamber of a Wurster coater and a cooperating probe of the present invention.

Referring to FIG. 1 in greater detail, there is shown a Wurster coating chamber 2 which consists of an outer continuous housing 4, an inner chamber 10, through which particles coated by the material delivered through nozzle 12 will travel upwardly and then come downwardly through the annular passage 14. The Wurster coater will typically have an overlying expansion chamber (not shown) and a filter (not shown) overlying the expansion chamber. The probe 20 of the present invention is shown with a single coated article 22 disposed within upwardly open recess 24 which has an enlarged portion 26 disposed at its entry in order to facilitate entry of the coated article 220. The probe 20 is preferably generally cylindrical and may be made of any suitable material, such as stainless steel, aluminum or plastic. An elongated passageway 30 receives a bundle of fiberoptic fibers 32 within protective sleeves 34, 37. Spectrometer means 38, which serves as a light source and receives and processes the reflected light, cooperates with the outer end of fiberoptic bundle. One set of fiberoptic fibers delivers light, which preferably is near infrared light to the end of the bundle located adjacent to the coated article 22. Reflected light is delivered by another group of fibers in the bundle 32 to the spectrometer means 38 wherein processing to determine coating thickness is effected in a manner to be described hereinafter.

It will be appreciated that in the embodiment illustrated in FIG. 1, inspection of the coated article which may be a coated drug unit is effected within the fluidized bed of such units on-line without the need to withdraw the specimen from the fluidized bed.

In one embodiment of the invention, the elongated probe 20, which in the form shown has a generally horizontal axis, may be rotated about that axis so as to cause the coated article 22 to be withdrawn after inspection from recess 24 under the influence of gravity. An opaque sleeve 37 is disposed around the fiberoptic bundle between sleeve 30 and spectrometer means 38 to resist entrance of stray light or loss of light.

Figure 2:
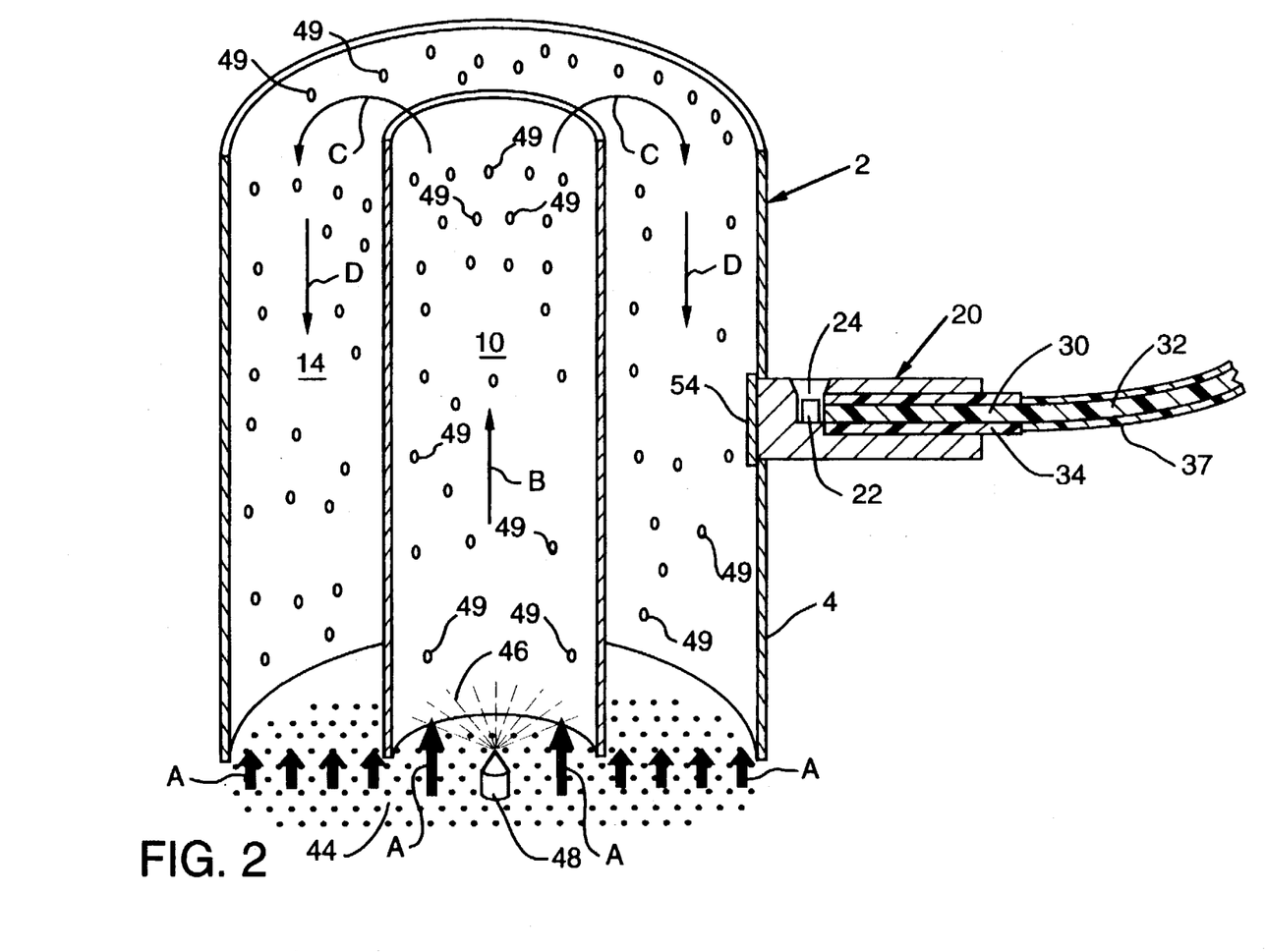
FIG. 2 is similar to FIG. 1, but shows additional details.

Referring to FIG. 2, there is shown an air distribution plate 44 in the lower region with air moving upwardly in the direction indicated by the arrows, such as those identified by the letter A under the influence of a suitable fan (not shown). The particles, some of which have been labelled 49, move in the direction of arrows B, C, and D and are coated with a coating material 46 emerging from a coating nozzle 48 and coating the particles which move upwardly within coating chamber 10. In this embodiment, the probe 20 has been moved axially to the right as compared with its position in FIG. 1 thereby exposing the coated article 22 so that it may be removed for inspecting at-line or in a remote location.

Secured to the free end of the probe 20 disposed within housing 4 is a stop member 54 which is of larger diameter than the opening in housing wall 4 through which the probe passes and thereby resists undesired full removal of the probe from the housing 2. If it is desired to permit full removal of the probe 20, stop member 54 may be eliminated.

While for convenience of disclosure herein, reference has been made in connection with the use of the probe of the present invention, in cooperation with a Wurster coating chamber, the invention is not so limited. For example, it may be employed with other sources of coated articles, such as a pan coater, for example.

Figure 3:
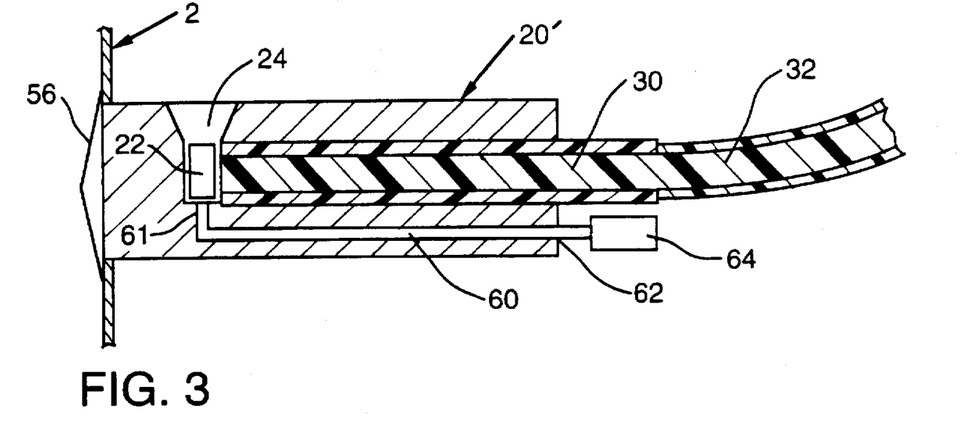
FIG. 3 is a cross-sectional illustration of a modified version of a probe of the present invention.

In the embodiment shown in FIG. 3, a port 60 formed within probe 20 has one end 61 communicating with the lower portion of recess 24 and another end 62 in communication with a reversible pump 64, such that with pump 64 operating in a first direction, pressurized air will be supplied to the lower portion of recess 24 to thereby urge the coated article 22 out of the recess 24. By operating the pump 64 in the reverse direction, suction will be applied to the lower portion of recess 24 to thereby tend to urge the coated article 22 into the recess 24 either during initial entry or during inspection. The probe end 56 in this view has a tapered configuration.

Figure 4:
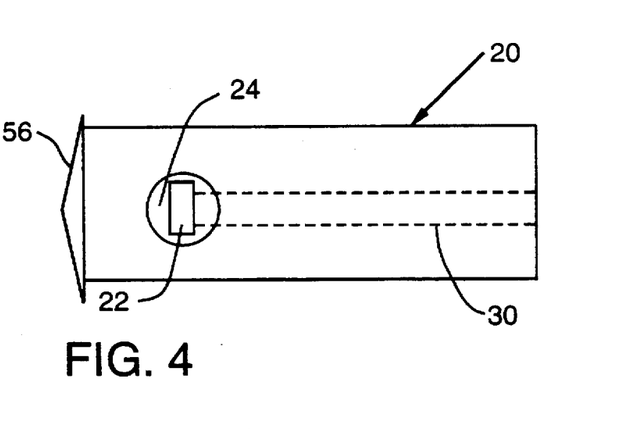
FIG. 4 is a top plan view of a probe of the present invention.

FIG. 4 is a top plan view of the probe 20 showing in phantom the fiberoptic receiving port 30, the recess 24 communicates with the outer periphery of the probe 20, and is oriented generally perpendicularly with respect to fiberoptic probe port 30. The coated article 22 is shown positioned within the recess 24. In general, it will be preferred to have all of the recess highly polished so as to facilitate entry and exit of the coated articles into and out of the recess.

Figure 5:
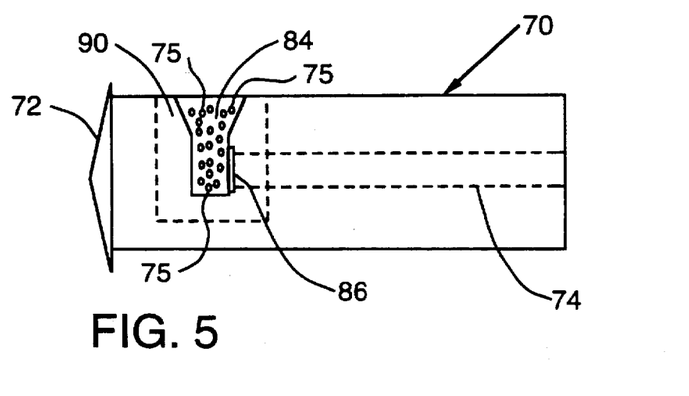
FIG. 5 is a front elevational view of a modified form of a probe of the invention employing inserts.

Referring to FIG. 5, another embodiment of the invention will be considered. The probe 70 has an end stop 72, a fiberoptic receiving port 74, and a recess 84 which is upwardly open. In this embodiment, the coated article is a plurality of particles 75 rather than a unitary coated article, such as 22. This embodiment contains two additional features. A first feature is a window 86 which will be interposed between recess 84 and fiberoptic receiving port 74. The window will serve to permit ready passage of light therethrough, but will resist the undesired passage of solid objects therethrough. The window might be made of any suitable material which is optically transparent, such as quartz or sapphire, or an appropriate glass, for example.

Another feature of this embodiment is that the recess 84 is defined within insert 90 which is a separate member which has been physically urged into friction fit with an insert receiving opening within the probe 70. An advantage of this embodiment is that when the probe is to be employed on more than one coated article having different size or shape, rather than providing a completely separate probe, one may need merely to remove one probe insert and substitute another. The inserts may be such as to be friction fit within the probe or may be secured by other suitable means, such as removable mechanical fastening means. In lieu of this approach, different size recesses 24, 84, may be provided by providing different probe needs which may be secured mechanically to the fiberoptic containing portion of the probe as by threaded securement or other demountable mechanical attachment.

Figure 6:
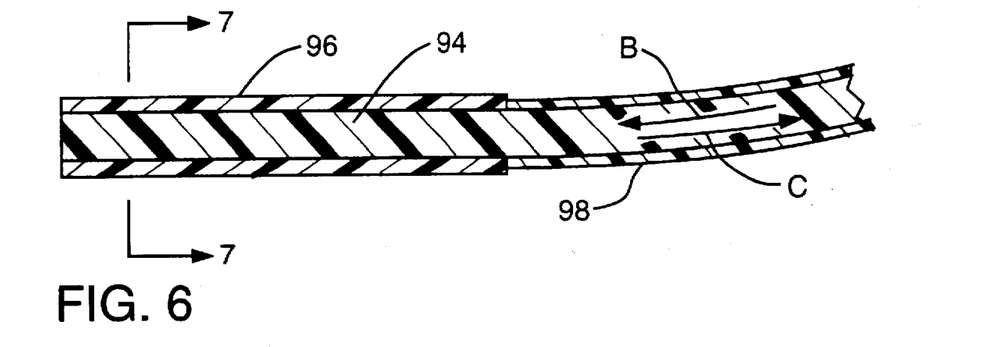
FIG. 6 is an illustration of a portion of the probe providing details of the fiberoptics.
Figure 7:
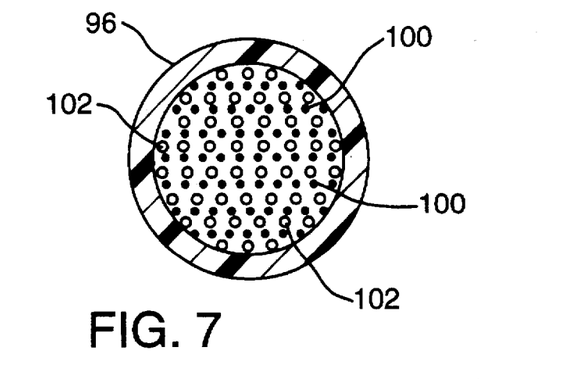
FIG. 7 is a cross-section of the fiberoptics taken through 7—7 of FIG. 6.

Referring to FIGS. 6 and 7, additional details of the preferred fiberoptic bundle will be considered. The fiberoptic bundle 94 has an opaque outer sleeve 96, a protective sheath 98 with the bundle portion shown to the right having fibers for transmitting light toward the coated article as indicated by arrow B and fibers for transmitting reflected light away from the coated article as indicated by arrow C. Shown schematically in FIG. 7 are the two groups of fibers which are intermingled in the embodiment shown with the solid black fibers 100 indicating the position of a group of transmitting or receiving fibers and the other fibers 102 indicating the opposite function fibers.

Figure 8:
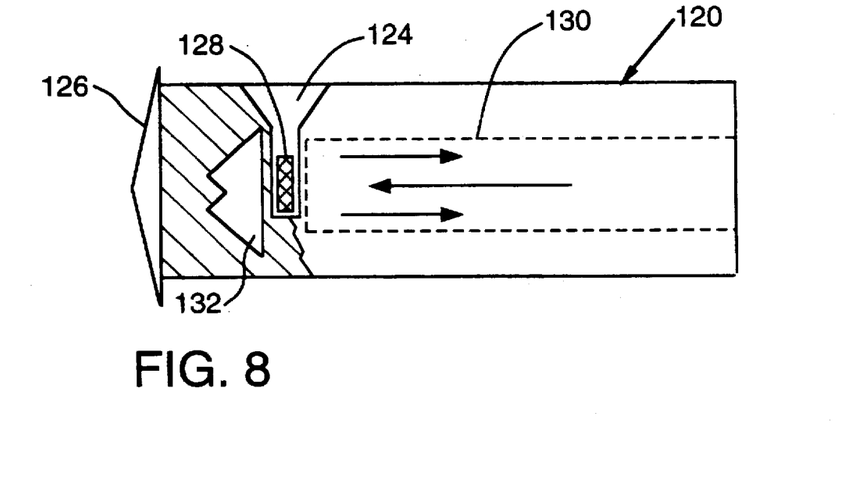
FIG. 8 is a partially schematic cross-sectional illustration of a modified form of the present invention.

A further embodiment of the invention will be considered in connection with FIG. 8 wherein a probe 120 has a recess 124, stop means 126, a coated article 128, and a fiberoptic bundle receiving passageway 130. For convenience of illustration, the left end of the passageway has been shown as spaced from the recess 124. It will generally be adjacent a window (not shown) or define part of the recess 124 in order to facilitate efficient light transfer. A structure disclosed in Drennen U.S. Pat. No. 5,214,227, the disclosure of which is incorporated herein by reference, which will facilitate illumination of the entire coated article by incorporation of reflective recess 132 may be employed. A suitable system for use in the embodiment of FIG. 8 is that sold under the trade designation "CAPCELL" from Optical Prototypes, Inc. of Mars, Penna.

Figure 9:
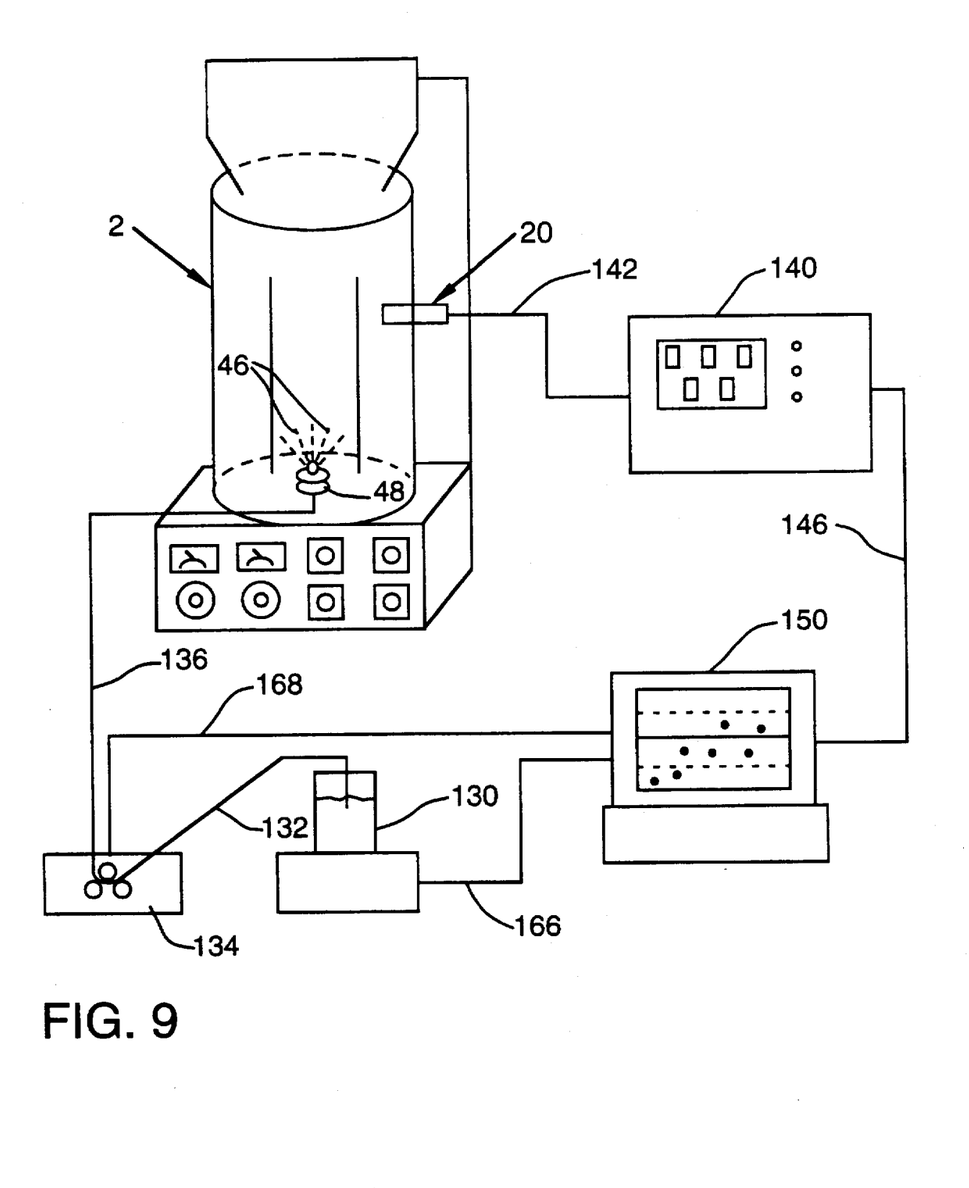
FIG. 9 is a partially schematic illustration of an overall system employing a probe of the present invention.

Referring to FIGS. 9 and 2, an overview of a preferred version of the system will be considered. As the probe of the present invention and its method of use are adapted for a wide variety of uses and various systems, it will be known to those skilled in the art that the full details of the system need not be provided. The Wurster coating chamber 2 receives the probe 20 with a coated article 22 (FIG. 2) positioned in the probe recess which is disposed within the housing 4. A suitable coating material is positioned within reservoir 130, which is an electric balance 131, which monitors the amount of coating material in reservoir 130. Reservoir 130, which has an outlet tube 132 operatively associated with pump 134, which through tube 136, delivers the material to nozzle 48 which sprays the material in the pattern shown generally by the number 46 so as to coat the upwardly moving particles (not shown). The spectrometer 140 is associated with the probe 20 through the optical fiber bundle 142. The spectrometer 140 produces an output signal on electrical lead 146 to microprocessor 150. In operation, the computer will have stored information regarding the desired extent of coating such that, as will be known to those skilled in the art, a comparison between the actual measured extent of coating and the desired extent of coating may be made in a quantitative or qualitative basis. An example of suitable software for use in this program is that available under the trade designation "SpeakEasy" from SpeakEasy Computing Corporation of Chicago, Ill. Information is delivered from spectrometer 140 to the microprocessor 150 over electrical lead 146. Microprocessor 140 sends control signals to the pump 134 over electrical lead 168.

It will be appreciated that in this manner effective control of the sampling and inspection process is provided.

Figure 10:
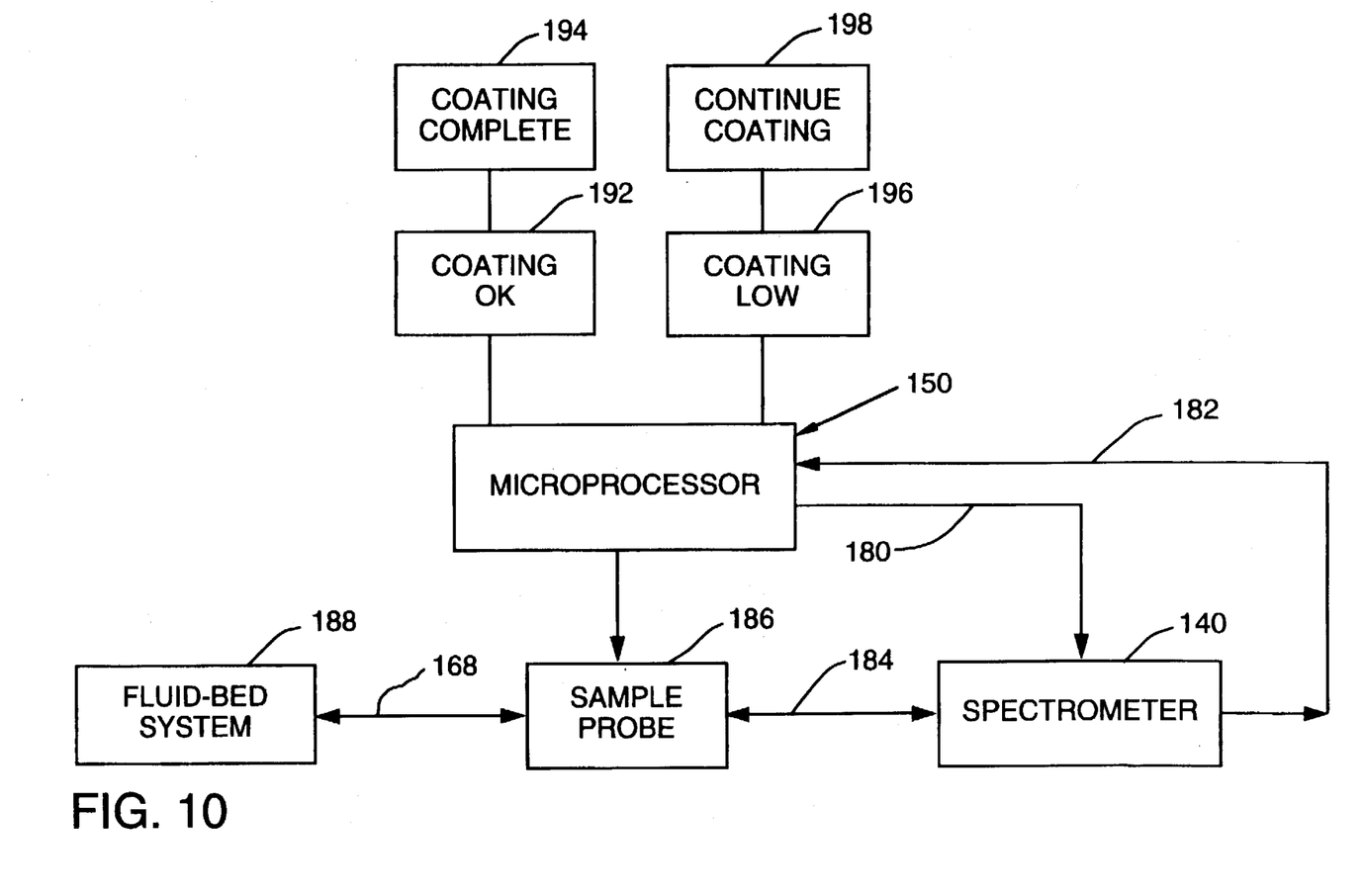
FIG. 10 is a schematic illustration showing the microprocessor and its interaction with other components of the system.

Referring to FIG. 10, the microprocessor 150 interacts with the spectrometer 140 which is the source of near infrared radiation over electrical leads 180, 182. The output from the light source, which forms a part of the spectrometer 140, is delivered by fiberoptic fibers 184 to the sample probe 186 and fiberoptic fibers 184 also serve to receive reflected light from the probe 186 over fiberoptic bundle 184. The sample probe 186 obtains a sample from the fluidized bed 188 over lead 168. In this embodiment, a servomechanism concept can be employed such that when the end point of the coating process is approved by the inspection process as in block 192, the coating process will be terminated 194 by the microprocessor 150 shutting off pump 134 (FIG. 9). When, however, the coating is not within specification 196, such as in being too thin, as indicated by block 196, the coating operation may continue 198.

Figure 11:
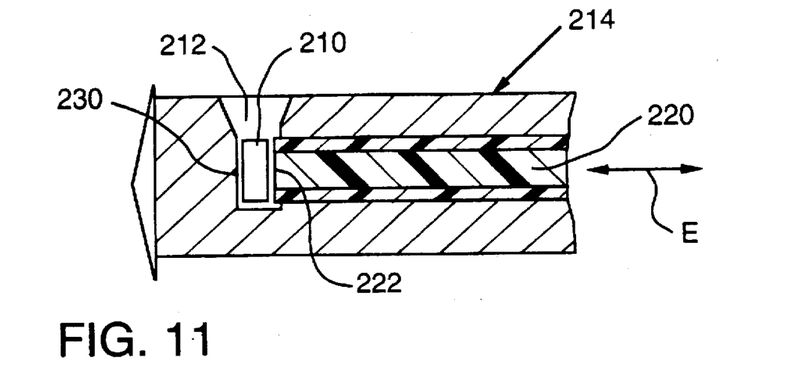
FIG. 11 is a fragmentary cross-sectional illustration of a sample securing means of the present invention.

Referring to FIG. 11, an embodiment of the invention wherein the coated article 210 is clamped within recess 212 of probe 214. The fiberoptic unit 220 is axially movable in the direction indicated by arrow E so as to permit clamping of coated article between the free end 222 of fiberoptic unit 220 and opposed recess defining wall 230 prior to inspection. This serves to position and restrain the coated article 210. Movement of the fiberoptic unit 220 may be effected manually or by suitable mechanical means, such as a threaded engagement between the fiberoptic unit 120 and another part of the probe 214, for example.

Figure 12:
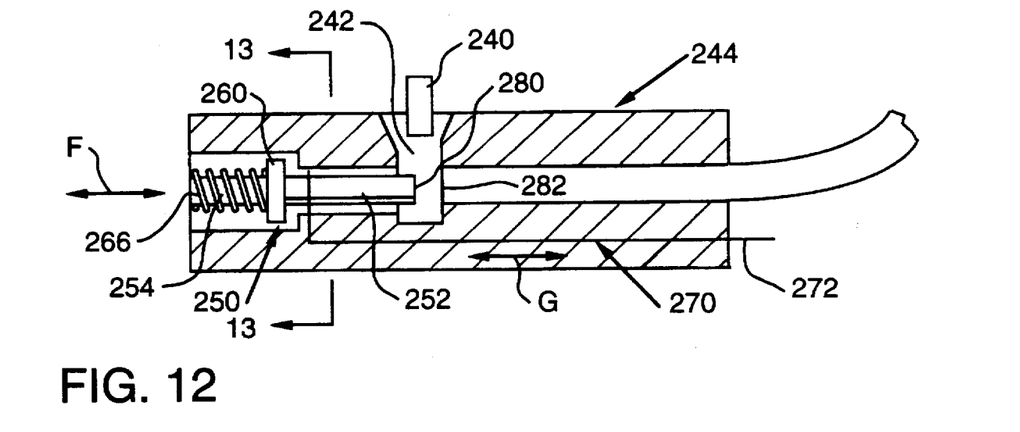
FIG. 12 is similar to FIG. 11, but shows a different type of sample securing means.
Figure 13:
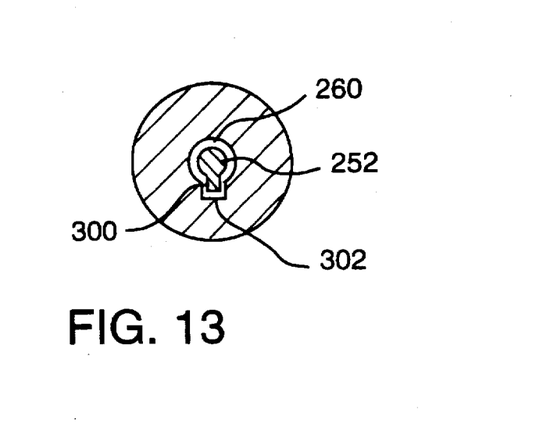
FIG. 13 is a cross-sectional illustration of the structure of FIG. 12 taken through 13—13.

In the embodiment of FIGS. 12 and 13, a unitary coated article 240 is received within recess 242 of probe 244. A rod 250 has a small diameter portion 252 and a large diameter portion 254 with an interposed annular radially enlarged portion 260. A coil spring 266 surrounds portions 254 and urges rod 250 to the right. The rod 250 reciprocates in the direction shown by arrow G. When rod 250 is in the left hand position, portion 252 does not project into recess 242. Operating member 270 moves in the direction indicated by arrow G. The free end 272 of operating member 270 projects to the right for manual engagement. The left end of operating member 250 engages the right side of enlarged portion 260. Pushing operating member 270 to the left moves rod 250 to the left to facilitate entry of coated article 240 into recess 242. Release of operating member 270 will cause rod 250 to move to the right and clamp coated article 240 between rod end 280 and wall 282 for positioning and restraint of coated article 240 during inspection.

As shown in FIG. 13, rod 250 has a projecting key 300 received within key way 302 to resist axial rotation of said rod 250.

While the preferred embodiments illustrate inspection with the probe being on-line or at-line in cooperation with coating equipment, the probe may be held manually and employed otherwise as disclosed herein.

The invention may be employed to inspect the extent of coating of intermediate products or product components as well as final products.

The invention may be employed to determine other characteristics such as granulation, drying, mixing and potency in drug layering, for example.

It will be appreciated, therefore, that the present invention has provided an improved means for efficiently and reliably on the sampling basis inspecting the coating on a coated article, such as a coated drug unit, for example. All of this may be accomplished either on-line, wherein the probe keeps a sample captive within the fluidized bed housing, or at-line or at a laboratory. The apparatus and associated invention are adapted to operate in a simple, but effective manner and in a preferred embodiment, delivers information regarding the extent of coating, such as thickness, for example, by fiberoptic means employing near infrared light which in turn cooperates with a spectrometer and a controlling microprocessor.

Whereas particular embodiments of the present invention have been described herein for purposes of illustration, it will be appreciated by those skilled in the art that numerous variations of the details may be made without departing from the invention as described in the appended claims.

We claim:

1. Apparatus for nondestructively inspecting a coated article to determine the extent of coating comprising
   a housing for containing and transporting said coated article,
   an elongated coated article receiving probe which is receivable within said housing,
   said probe having a recess in communication with the exterior of said probe for receiving said coated article,
   a passageway for receiving fiberoptic means in communication with said coated article receiving recess,
   spectrometer means for analyzing coating thickness information received from said fiberoptic means, and
   fiberoptic means in optical communication with said article receiving recess for delivering light to a coated article disposed therein and receiving reflected light therefrom and delivering said reflected light to said spectrometer means.

2. The apparatus of claim 1 including
   said recess being of a size and shape to receive a coated article therein.

3. The apparatus of claim 1 including
   said recess being of a configuration to receive a coated article selected from the group consisting of a drug unit, an agricultural seed and a coated confection.

4. The apparatus of claim 1 including
   said housing being structured to transport said coated article in a fluidized bed.

5. The apparatus of claim 1 including
   said recess having an enlarged portion at the entry portion thereof to facilitate capture of a said coated article in said recess.

6. The apparatus of claim 5 including
   said probe being axially rotatable to facilitate removal of said coated article from said recess after said inspection.

7. The apparatus of claim 5 including
   said probe being axially movable to remove a coated article from said housing for inspection.

8. The apparatus of claim 5 including
   window means disposed between said fiberoptic means and said recess for permitting passage of light therethrough, but resisting passage of solids therethrough.

9. The apparatus of claim 5 including
   said recess being formed in a removable insert to permit substitution of another insert with a recess of a different configuration.

10. The apparatus of claim 5 including
    pneumatic means for urging said coated article out of said recess under the influence of pressure after said inspection.

11. The apparatus of claim 5 including
    microprocessor means for controlling said apparatus.

12. The apparatus of claim 11 including
    means for providing near-infrared light to said fiberoptic means for delivery to said coated article.

13. The apparatus of claim 12 including
    said microprocessor means being adapted to be operatively associated with a coating system which coats said coated articles, and
    said microprocessor means having means for controlling the coating system responsive to said inspection.

14. The apparatus of claim 5 including
    said passageway being disposed generally longitudinally in said probe, and
    said recess being oriented generally perpendicular to said passageway.

15. The apparatus of claim 14 including
    said probe being generally cylindrical.

16. The apparatus of claim 1 including
    said recess being of such size and shape as to correspond substantially in size and shape to said coated article and to permit insertion of said coated article into said recess in close fitting relationship.

17. The apparatus of claim 10 including
    said pneumatic means having means for applying suction to said recess to urge said coated article into said recess.

18. The apparatus of claim 7 including
    stop means disposed on said probe for resisting complete removal of said probe from said housing.

19. The apparatus of claim 16 including
    means for positioning said coated article within said recess during said inspection.

20. The apparatus of claim 19 including said means for positioning including clamping means, and said clamping means having movable elements cooperating with a recess defining wall to effect said clamping.

21. The apparatus of claim 1 including said housing containing means for coating said articles.

22. The apparatus of claim 20 including said coated article having been coated by a coating system selected from the group consisting of a fluidized bed and a pan coater.

23. The apparatus of claim 3 including said recess being of a configuration to receive at least one of (a) a unitary coated article and (b) a plurality of coated articles.

24. A method of nondestructively inspecting coated articles to determine the extent of coating comprising providing a source of said coated articles, a housing for containing and transporting said coated articles and an elongated probe receivable in said housing and having a recess for receiving coated articles with said recess being in communication with the exterior of said probe and a passageway in communication with said recess having fiberoptic means disposed therein, introducing a said coated article into said recess, delivering light through said fiberoptic means to said coated article, receiving reflected light from said coated article, and delivering said reflected light to processing means for determining the extent of coating.

25. The method of claim 24 including providing said recess of a size and shape so as to receive said coated article in relative close-fitting relationship.

26. The method of claim 25 including employing said method to inspect a coated article selected from the group consisting of a coated drug unit, a coated agricultural seed and a coated confection.

27. The method of claim 26 including transporting a said coated drug unit in a fluidized bed, and introducing a said coated drug unit from a fluidized bed into said recess prior to effecting said inspection.

28. The method of claim 27 including providing an enlargement in said recess adjacent the entry portion thereof to facilitate capture of a said coated drug unit therein.

29. The method of claim 28 including subjecting said probe to axial rotation after inspection to facilitate removal of said coated drug unit from said recess.

30. The method of claim 28 including employing pneumatic means for urging said coated drug unit out of said recess after said inspection.

31. The method of claim 30 including employing said pneumatic means to apply a vacuum to said recess to urge said coated drug unit into said recess.

32. The method of claim 24 including employing spectrometer means for analyzing coating thickness information received from said fiberoptic means.

33. The method of claim 32 including employing microprocessor means to control inspection of a coated drug unit inspection.

34. The method of claim 33 including providing said recess in a removable probe member so that a different member may be employed when said inspection will involve coated drug units of a different size.

35. The method of claim 34 including creating a fluidized bed suspension for delivery of said drug units to said probe member, and employing microprocessor means for controlling said fluidized bed suspension and delivery of said coated drug units.

36. The method of claim 35 including performing said inspection on-line while said coated drug unit is disposed within said housing.

37. The method of claim 35 including removing said coated drug unit from said housing of said probe prior to effecting said inspection.

38. The method of claim 24 including employing said housing as said source of said coated articles, and coating said coated articles in said housing.

39. The method of claim 38 including effecting said coating in a system selected from the group consisting of a fluidized bed and a pan coater.

40. The method of claim 38 including clamping said coated article during said inspection.

41. The method of claim 24 including employing said method to inspect a unitary coated article.

42. The method of claim 24 including employing said method to inspect a plurality of coated particles.

* * * * *